(12) United States Patent
Chun et al.

(10) Patent No.: US 7,999,459 B2
(45) Date of Patent: Aug. 16, 2011

(54) ORGANIC LIGHT EMITTING DIODE AND METHOD OF MANUFACTURING THE SAME

(75) Inventors: Min-Seung Chun, Suwon-si (KR);
Dong-Heon Kim, Suwon-si (KR);
Jae-Hyun Kwak, Suwon-si (KR);
Jung-Ha Son, Suwon-si (KR);
Mi-Kyung Kim, Suwon-si (KR);
Kwan-Hee Lee, Suwon-si (KR)

(73) Assignee: Samsung Mobile Display Co., Ltd., Yongin-city (KR)

( * ) Notice: Subject to any disclaimer, the term of this patent is extended or adjusted under 35 U.S.C. 154(b) by 203 days.

(21) Appl. No.: 12/360,000

(22) Filed: Jan. 26, 2009

(65) Prior Publication Data

US 2009/0189521 A1    Jul. 30, 2009

(30) Foreign Application Priority Data

Jan. 28, 2008    (KR) .................. 10-2008-0008722

(51) Int. Cl.
*H01J 1/63*    (2006.01)
*B05D 5/06*    (2006.01)

(52) U.S. Cl. .................. 313/504; 427/66

(58) Field of Classification Search .......... None
See application file for complete search history.

(56) References Cited

U.S. PATENT DOCUMENTS

| | | |
|---|---|---|
| 5,486,406 A | 1/1996 | Shi |
| 6,670,053 B2 | 12/2003 | Conley |
| 6,878,469 B2 | 4/2005 | Yoon et al. |
| 2003/0235713 A1 | 12/2003 | Suzuki et al. |
| 2004/0209117 A1 | 10/2004 | Aziz et al. |
| 2005/0084713 A1 | 4/2005 | Kido et al. |
| 2005/0260442 A1 | 11/2005 | Yu et al. |
| 2006/0008674 A1 | 1/2006 | Yu et al. |
| 2007/0092754 A1* | 4/2007 | Begley et al. ............. 428/690 |
| 2007/0200490 A1 | 8/2007 | Kawamura et al. |
| 2008/0032123 A1* | 2/2008 | Spindler et al. ............ 428/336 |
| 2008/0111473 A1 | 5/2008 | Kawamura et al. |
| 2009/0206740 A1 | 8/2009 | Chun et al. |
| 2009/0233125 A1 | 9/2009 | Choi et al. |

FOREIGN PATENT DOCUMENTS

CN    1261760 A    8/2000

(Continued)

OTHER PUBLICATIONS

Korean Office action dated Oct. 23, 2009, for related Korean priority application KR 10-2008-0008721, noting listed references in this IDS.

(Continued)

*Primary Examiner* — D. Lawrence Tarazano
*Assistant Examiner* — Camie S Thompson
(74) *Attorney, Agent, or Firm* — Christie, Parker & Hale, LLP (57) ABSTRACT

The invention is directed to organic light emitting diodes (OLEDs) and methods of manufacturing the same. According to embodiments of the invention, an improved electron transport layer (ETL) reduces the driving voltage and current consumption of the OLED, and increase luminous efficiency and lifespan. The OLED includes a first electrode, an organic layer on the first electrode and including an emission layer (EML) and an ETL, and a second electrode on the organic layer.

18 Claims, 2 Drawing Sheets

FOREIGN PATENT DOCUMENTS

| | | | |
|---|---|---|---|
| CN | 1898355 | A | 1/2007 |
| EP | 1 265 298 | A2 | 12/2002 |
| EP | 1 691 586 | A1 | 8/2006 |
| EP | 1 734 038 | A1 | 12/2006 |
| JP | 10-270171 | | 10/1998 |
| JP | 10-270172 | | 10/1998 |
| JP | 11-329734 | | 11/1999 |
| JP | 2000-344691 | | 12/2000 |
| JP | 2005-123094 | | 5/2005 |
| JP | 2005-515233 | T | 5/2005 |
| JP | 2005-174675 | | 6/2005 |
| JP | 2006-028175 | | 2/2006 |
| KR | 1999-0075849 | | 10/1999 |
| KR | 2001-0080629 | | 8/2001 |
| KR | 10-0317284 | | 11/2001 |
| KR | 2002-0063139 | | 8/2002 |
| KR | 10-2003-0014119 | | 2/2003 |
| KR | 10-2003-0067773 | | 8/2003 |
| KR | 10-0434626 | | 5/2004 |
| KR | 10-2006-0096057 | | 9/2006 |
| KR | 10-2007-0068147 | | 6/2007 |
| KR | 10-2007-0088978 | | 8/2007 |
| WO | WO 2005/097756 | A1 | 10/2005 |
| WO | WO 2006/127315 | A2 | 11/2006 |
| WO | WO 2006/138075 | A2 | 12/2006 |
| WO | WO 2007/021117 | A1 | 2/2007 |
| WO | WO 2007/050331 | A1 | 5/2007 |
| WO | WO 2007/052985 | A1 | 5/2007 |

OTHER PUBLICATIONS

SIPO Office action dated Jan. 15, 2010, for corresponding Chinese Patent application 200910008531.4, with English translation, noting listed references in this IDS.

European Search Report dated Jun. 3, 2009, for corresponding European application 09250233.5, noting European references, KR 2007/0088978 and WO 2007/050331 listed in this IDS.

KIPO Office action dated Apr. 28, 2008, in corresponding U.S. Appl. No. 12/048,704, for Korean priority application 10-2007-0025072, noting U.S. Patent 6,670,053 listed in this IDS.

European Search Report dated Dec. 15, 2008, in corresponding U.S. Appl. No. 12/048,704, for European application 08152670.9, noting WO 2007/021117, WO 2007/052985 references, and U.S. Publication 2005/0260442 listed in this IDS.

European Search Report dated Mar. 30, 2009, in corresponding U.S. Appl. No. 12/048,704, for European application 08152670.9, noting International (WO) references, and U.S. Publications 2005/0260442 and 2003/0235713 listed in this IDS.

Korean Patent Abstracts, Publication No. 2000-67671, dated Nov. 25, 2000, corresponds to Korean reference 10-0317284 listed above.

Chinese Office action dated Jun. 21, 2010 for corresponding Chinese application No. 200910008531.4 with English translation.

* cited by examiner

ORGANIC LIGHT EMITTING DIODE AND METHOD OF MANUFACTURING THE SAME

CROSS-REFERENCE TO RELATED APPLICATION

This application claims priority to and the benefit of Korean Patent Application No. 2008-0008722, filed Jan. 28, 2008 in the Korean Intellectual Property Office, the entire content of which is incorporated herein by reference.

BACKGROUND OF THE INVENTION

1. Field of the Invention

The present invention relates to organic light emitting diodes (OLEDs) and methods of manufacturing the same.

2. Description of the Related Art

Organic light emitting diodes (OLEDs) are self-emissive displays that may be lightweight and thin, and fabricated by simple processes using simple components. Also, OLEDs have high resolution and wide viewing angles, and can embody complete moving images with high color purity. In addition, OLEDs have appropriate electrical characteristics for mobile display devices because OLEDs consume little power and drive at low voltages.

In a conventional OLED, a pixel electrode is provided, an organic layer including an emission layer (EML) is disposed on the pixel electrode, and an opposite electrode is disposed on the organic layer.

To facilitate the transfer of holes and electrons from the pixel electrode and the opposite electrode to the EML, the organic layer may further include at least one layer selected from hole injection layers (HILs), hole transport layers (HTLs), and electron blocking layers (EBLs) between the pixel electrode and the EML. In addition, the organic layer may further include at least one layer selected from hole blocking layers (HBLs), electron transport layers (ETLs), and electron injection layers (EILs) between the EML and the opposite electrode.

However, the ETL is typically formed of a single organic material. As a result, the OLED including the ETL needs to drive at a high driving voltage and consume a large current, imparting poor luminous efficiency and insufficient lifespan. Therefore, high quality OLEDs are difficult to achieve.

SUMMARY OF THE INVENTION

Embodiments of the present invention provide an organic light emitting diode (OLED) and a method of manufacturing the same. In one embodiment, an improved electron transport layer (ETL) reduces driving voltage and current consumption, thereby increasing the luminous efficiency and lifespan of the OLED.

According to an embodiment of the present invention, an OLED includes a first electrode, an organic layer on the first electrode and including an emission layer and an electron transport layer (ETL), and a second electrode on the organic layer. The ETL may include an organic metal complex including an alkali metal and a compound represented by Formula 1, below.

Formula 1

In Formula 1, each of $R_1$ to $R_7$ and $R_{16}$ to $R_{22}$ is independently selected from hydrogen atoms, phenyl groups, indenyl groups, naphthalenyl groups, benzofuranyl groups, benzothiophenyl groups, indolyl groups, benzimidazolyl groups, benzothiazolyl groups, purinyl groups, quinolinyl groups, isoquinolinyl groups, coumarinyl groups, cinnolinyl groups, quinoxalinyl groups, azulenyl groups, fluorenyl groups, dibenzofuranyl groups, carbazolyl groups, anthracenyl groups, phenanthrenyl groups, aziridinyl groups, 1,10-phenanthrolinyl groups, phenothiazinyl groups, and pyrenyl groups.

At least one of $R_8$ to $R_{15}$ is an aromatic heterocyclic group having 3 to 30 carbon atoms in which at least one ring of the group has two nitrogen atoms. Each of the rest of $R_8$ to $R_{15}$ is independently selected from hydrogen atoms, phenyl groups, indenyl groups, naphthalenyl groups, benzofuranyl groups, benzothiophenyl groups, indolyl groups, benzothiazolyl groups, quinolinyl groups, isoquinolinyl groups, coumarinyl groups, azulenyl groups, fluorenyl groups, dibenzofuranyl groups, carbazolyl groups, anthracenyl groups, phenanthrenyl groups, aziridinyl groups, phenothiazinyl groups, and pyrenyl groups. A compound in which $R_1$ to $R_8$, $R_{11}$ and $R_{12}$, and $R_{15}$ to $R_{22}$ are hydrogen atoms, and one of $R_9$, $R_{10}$, $R_{13}$ and $R_{14}$ is the aromatic heterocyclic group having 3 to 30 carbon atoms in which at least one ring of the group has two nitrogen atoms is specially excluded.

Alternatively, one of $R_8$ to $R_{15}$ may be a phenyl group bonded to an aromatic heterocyclic group having 3 to 30 carbon atoms in which at least one ring in the group has two nitrogen atoms. Each of the rest of $R_8$ to $R_{15}$ is independently selected from hydrogen atoms, phenyl groups, indenyl groups, naphthalenyl groups, benzofuranyl groups, benzothiophenyl groups, indolyl groups, benzothiazolyl groups, quinolinyl groups, isoquinolinyl groups, coumarinyl groups, azulenyl groups, fluorenyl groups, dibenzofuranyl groups, carbazolyl groups, anthracenyl groups, phenanthrenyl groups, aziridinyl groups, phenothiazinyl groups, and pyrenyl groups.

According to another embodiment of the present invention, a method of manufacturing an OLED includes providing a first electrode, forming an organic layer including an EML and an ETL on the first electrode, and forming a second electrode on the organic layer. The ETL is formed by co-depositing an organic metal complex including an alkali metal and a compound represented by Formula 1, above.

BRIEF DESCRIPTION OF THE DRAWINGS

These and other features of the present invention will be better understood by reference to the following detailed description when considered in conjunction with the attached drawings in which.

DETAILED DESCRIPTION OF THE INVENTION

The present invention will now be described with reference to the accompanying drawings, in which exemplary embodiments of the invention are shown. In the drawings, the thicknesses of layers and regions are exaggerated for clarity. Like reference numerals are used to denote like elements throughout the specification.

Figure 1:
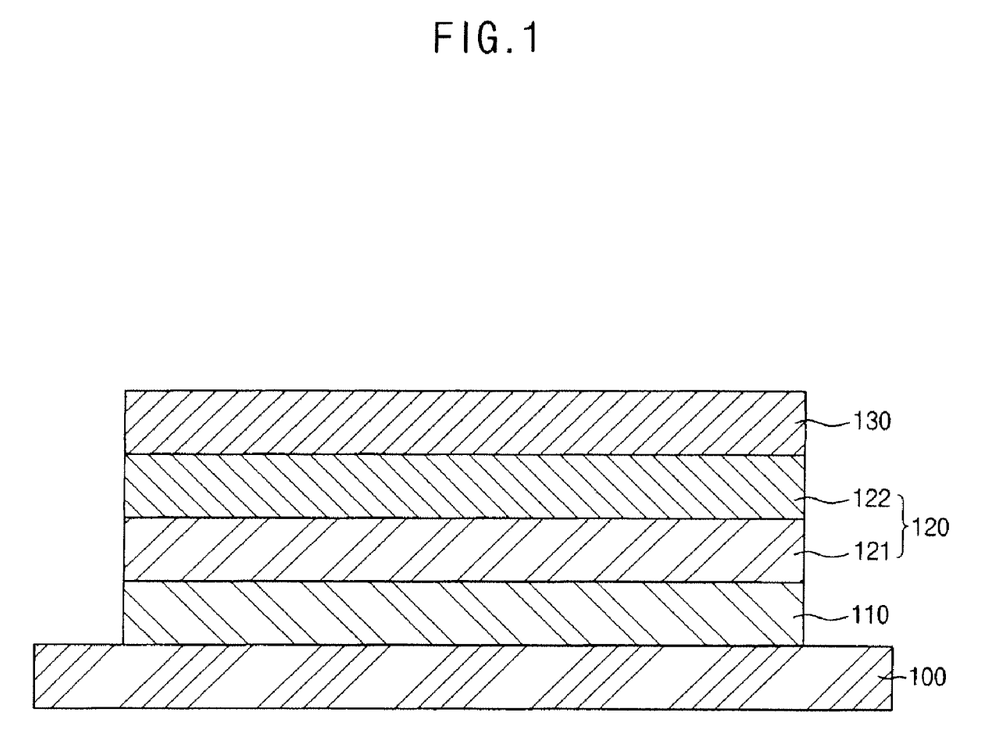
FIG. 1 is a cross-sectional view of an organic light emitting diode (OLED) according to an embodiment of the present invention.

FIG. 1 is a cross-sectional view of an organic light emitting diode (OLED) according to an embodiment of the present invention. Referring to FIG. 1, a substrate 100 is provided. The substrate 100 may be glass, plastic, or steel use stainless (SUS). The substrate 100 may include at least one thin film transistor (TFT) (not shown) connected to a first electrode 110.

The first electrode 110 is disposed on the substrate 100. The first electrode 110 may be an anode, which may be a transparent electrode or a reflective electrode. When the first electrode 110 is a transparent electrode, it may be an indium tin oxide (ITO) layer, an indium zinc oxide (IZO) layer, a tin oxide (TO) layer, or a zinc oxide (ZnO) layer. When the first electrode 110 is a reflective electrode, it may include a reflective layer and a transparent layer. The reflective layer may be formed of silver (Ag), aluminum (Al), chromium (Cr), molybdenum (Mo), tungsten (W), titanium (Ti), gold (Au), palladium (Pd), or an alloy thereof, and the transparent layer may be formed of ITO, IZO, TO, or ZnO. The first electrode 110 may be formed by sputtering, vapor phase deposition, ion beam deposition, electron beam (e-beam) deposition, or laser ablation.

Thereafter, an organic layer 120, including an emission layer (EML) 121 and an electron transport layer (ETL) 122, is disposed on the first electrode 110. The EML 121 may be a phosphorescent EML or a fluorescent EML. When the EML 121 is a fluorescent EML, it may include a host selected from 8-trishydroxyquinoline aluminum (Alq3), distyrylarylene (DSA) and derivatives thereof, distyrylbenzene (DSB) and derivatives thereof, DPVBi (4,4'-bis(2,2'-diphenyl vinyl)-1, 1'-biphenyl) and derivatives thereof, spiro-DPVBi, and spiro-6P (spiro-sexyphenyl). Also, the fluorescent EML 121 may include a dopant selected from styrylamine, perylene, and distyrylbiphenyl (DSBP).

When the EML 121 is a phosphorescent EML, it may include a host selected from arylamines, carbazoles, and spiros. Nonlimiting examples of suitable hosts for the EML 121 include CBP(4,4-N,N dicarbazole-biphenyl) and derivatives thereof, mCP(N,N-dicarbazolyl-3,5-benzene) and derivatives thereof, and spiro derivatives. Also, the phosphorescent EML 121 may further include a dopant, which may include a phosphorescent organic metal complex having a central metal atom selected from Ir, Pt, Tb, and Eu. Nonlimiting examples of suitable phosphorescent organic metal complexes include PQIr, PQIr(acac), PQ2Ir(acac), PIQIr(acac), and PtOEP.

The ETL 122 is disposed on the EML 121. In one embodiment, the ETL 122 may include an organic metal complex including an alkali metal and a compound represented by Formula 1, below.

Formula 1

In Formula 1, each of $R_1$ to $R_7$ and $R_{16}$ to $R_{22}$ is independently selected from hydrogen atoms, phenyl groups, indenyl groups, naphthalenyl groups, benzofuranyl groups, benzothiophenyl groups, indolyl groups, benzimidazolyl groups, benzothiazolyl groups, purinyl groups, quinolinyl groups, isoquinolinyl groups, coumarinyl groups, cinnolinyl groups, quinoxalinyl groups, azulenyl groups, fluorenyl groups, dibenzofuranyl groups, carbazolyl groups, anthracenyl groups, phenanthrenyl groups, aziridinyl groups, 1,10-phenanthrolinyl groups, phenothiazinyl groups, and pyrenyl groups.

At least one of $R_8$ to $R_{15}$ is an aromatic heterocyclic group having 3 to 30 carbon atoms in which at least one ring of the group has two nitrogen atoms. Each of the rest of $R_8$ to $R_{15}$ is independently selected from hydrogen atoms, phenyl groups, indenyl groups, naphthalenyl groups, benzofuranyl groups, benzothiophenyl groups, indolyl groups, benzothiazolyl groups, quinolinyl groups, isoquinolinyl groups, coumarinyl groups, azulenyl groups, fluorenyl groups, dibenzofuranyl groups, carbazolyl groups, anthracenyl groups, phenanthrenyl groups, aziridinyl groups, phenothiazinyl groups, and pyrenyl groups. A compound in which $R_1$ to $R_8$, $R_{11}$ and $R_{12}$, and $R_{15}$ to $R_{22}$ are hydrogen atoms, and one of $R_9$, $R_{10}$, $R_{13}$ and $R_{14}$ is the aromatic heterocyclic group having 3 to 30 carbon atoms in which at least one ring of the group has two nitrogen atoms is specially excluded.

Alternatively, one of $R_8$ to $R_{15}$ may be a phenyl group bonded to an aromatic heterocyclic group having 3 to 30 carbon atoms in which at least one ring of the group has two nitrogen atoms. Each of the rest of $R_8$ to $R_{15}$ is independently selected from hydrogen atoms, phenyl groups, indenyl groups, naphthalenyl groups, benzofuranyl groups, benzothiophenyl groups, indolyl groups, benzothiazolyl groups, quinolinyl groups, isoquinolinyl groups, coumarinyl groups, azulenyl groups, fluorenyl groups, dibenzofuranyl groups, carbazolyl groups, anthracenyl groups, phenanthrenyl groups, aziridinyl groups, phenothiazinyl groups, and pyrenyl groups.

The aromatic heterocyclic group having 3 to 30 carbon atoms in which at least one ring of the group has two nitrogen atoms may be selected from imidazolyl groups, benzimidazolyl groups, pyrazolyl groups, pyrazolinyl groups, pyrazolidinyl groups, oxadiazolyl groups, thiadiazolyl groups, pyridazinyl groups, pyrimidinyl groups, piperazinyl groups, purinyl groups, cinnolinyl groups, quinoxalinyl groups, and phenanthrenyl groups.

The organic metal complex including the alkali metal may include lithium quinolate or sodium quinolate.

The ETL 122 may include the organic metal complex including the alkali metal in an amount ranging from about 10 to about 60% by weight. The organic metal complex including the alkali metal has a high electron affinity, enabling it to interact with lone electron pairs from the two nitrogen atoms of the aromatic heterocyclic group (corresponding to one of $R_8$ to $R_{15}$ in Formula 1). Alternatively, the organic metal complex (having high electron affinity) may interact with lone electron pairs from the two nitrogen atoms of the aromatic heterocyclic group which is bonded to a phenyl group (positioned at one of $R_8$ to $R_{15}$ in Formula 1). The interaction between the organic metal complex and the lone electron pairs of the nitrogen atoms greatly increases the efficiency of transport and injection of electrons to the EML 121.

The ETL 122 may be formed by co-depositing the organic metal complex including the alkali metal and the compound of Formula 1.

As described above, the interaction between the organic metal complex including the alkali metal (having high electron affinity) and the lone electron pairs of the two nitrogen atoms of the aromatic heterocyclic group yields great improvements in the efficiency of transport and injection of electrons to the EML 121 as compared to conventional ETLs formed of a single organic material. As a result, the driving voltage and current consumption of the OLED can be reduced, and the luminous efficiency and lifespan of the OLED can be increased. In addition, since the ETL 122 also has an electron injection characteristic, the manufacturing process can be simplified by omitting the need to form an additional electron injection layer (EIL).

To elevate the efficiency of electron and hole injection to the EML 121, and the efficiency of electron and hole recombination in the EML 121, the organic layer 120 may further include at least one layer selected from hole injection layers (HILs), hole transport layer (HTLs), electron blocking layers (EBLs), hole blocking layers (HBLs), and EILs.

The HIL may facilitate the injection of holes into the EML 121 and increase the lifespan of the OLED. The HIL may be formed of an arylamine compound or starburst amine. Non-limiting examples of suitable materials for the HIL include 4,4',4"-tris(N-3-methylphenyl-N-phenyl-amino)-triphenylamine(m-MTDATA), 1,3,5-tris[4-(3-methyl-phenyl-phenyl-amino)phenyl]benzene(m-MTDATB), and copper phthalocyanine (CuPc).

The HTL may be formed of an arylene diamine derivative, a starburst compound, a biphenyl diamine derivative having a spiro group, or a ladder compound. Nonlimiting examples of suitable materials for the HTL include N,N'-diphenyl-N,N'-bis(3-methylphenyl)-1,1'-biphenyl-4,4'-diamine (TPD) and 4,4'-bis[N-(1-naphthyl-1-)-N-phenyl-amino]-biphenyl (NPB).

The EBL may inhibit the diffusion of excitons generated in the EML 121 during driving of the OLED. The EBL may be formed of BAlq, BCP, CF-X, 3-(4-biphenyl)-4-phenyl-5-(4-tert-butylphenyl)-1,2,4-triazole (TAZ), or spiro-TAZ.

The HBL may inhibit the transport of holes into the EIL when hole mobility is higher than electron mobility in the EML 121. The HBL may be formed of 2-(4-biphenyl)-5-(4-butylphenyl)-1,3,4-oxadiazole (PBD), spiro-PBD, or TAZ.

The EIL may be formed of a 1,3,4-oxadiazole derivative, a 1,2,4-triazole derivative, or LiF.

Also, the organic layer 120 may be formed by vacuum evaporation, inkjet printing, or laser induced thermal imaging (LITI).

A second electrode 130 is disposed on the ETL 122. The second electrode 130 may be a cathode, which may be a transmissive electrode or a reflective electrode. When the second electrode 130 is a transmissive electrode, it may be formed of a conductive metal having a low work function. For example, the metal may be selected from Mg, Ca, Al, Ag, and alloys thereof. The second electrode 130 may be formed to a thickness sufficient to transmit light. When the second electrode 130 is a reflective electrode, it may be formed to thickness sufficient to reflect light.

The following Experimental Examples are provided for illustrative purposes only, and do not limit the scope of the present invention.

Experimental Example 1

A first electrode was formed of ITO to a thickness of about 130 nm. Thereafter, an HIL was formed of IDE-406 (obtained from Idemitsu Co.) on the first electrode to a thickness of about 210 nm, and an HTL was formed of NPB to a thickness of about 20 nm. A red EML was formed on the HTL to a thickness of about 40 nm using a mixture of CBP as a host and 15% by weight $Ir(piq)_3$ as a dopant. An ETL was formed on the red EML. Specifically, 50% by weight of lithium quinolate as an organic metal complex containing an alkali metal, and 50% by weight of a compound of Formula 1 were co-deposited to a thickness of about 30 nm. In the compound of Formula 1, $R_9$ is a phenyl group to which a benzimidazolyl group is bonded, and each of $R_1$ to $R_8$ and $R_{10}$ to $R_{22}$ is hydrogen. Subsequently, a second electrode was formed on the ETL. To form the second electrode, an MgAg layer was formed to a thickness of about 16 nm, and an Al layer was formed on the MgAg layer to a thickness of about 100 nm.

Formula 1

Comparative Example 1

An OLED was prepared as in Experimental Example 1 except that the ETL was formed to a thickness of 30 nm and included only the compound of Formula 1.

The driving voltage, current consumption, luminance, and luminous efficiency of each of the OLEDs manufactured according to Experimental Example 1 and Comparative Example 1 were measured, and the results are shown in Table 1.

TABLE 1

|  | Driving voltage (V) | Current consumption (mA/cm$^2$) | Luminance (Cd/m$^2$) | Luminous efficiency (Cd/A) |
| --- | --- | --- | --- | --- |
| Experimental Example 1 | 3.593 | 5.067 | 800 | 15.834 |
| Comparative Example 1 | 4.816 | 6.960 | 800 | 11.484 |

Referring to Table 1, the driving voltage, current consumption, and luminous efficiency at the same luminance of the OLEDs according to Experimental Example 1 and Comparative Example 1 were compared. When the ETL included a mixture of the compound of Formula 1 containing a benzimidazolyl group (which is an aromatic heterocyclic group having 3 to 30 carbon atoms and at least one ring with two nitrogen atoms) and lithium quinolate (which is an organic metal complex containing an alkali metal), as in Experimental Example 1, driving voltage was reduced by about 1.2V, current consumption was reduced by about 1.9 mA/cm², and luminous efficiency was increased by about 4.35 Cd/A (about a 27% increase over the OLED according to Comparative Example 1).

Figure 2:
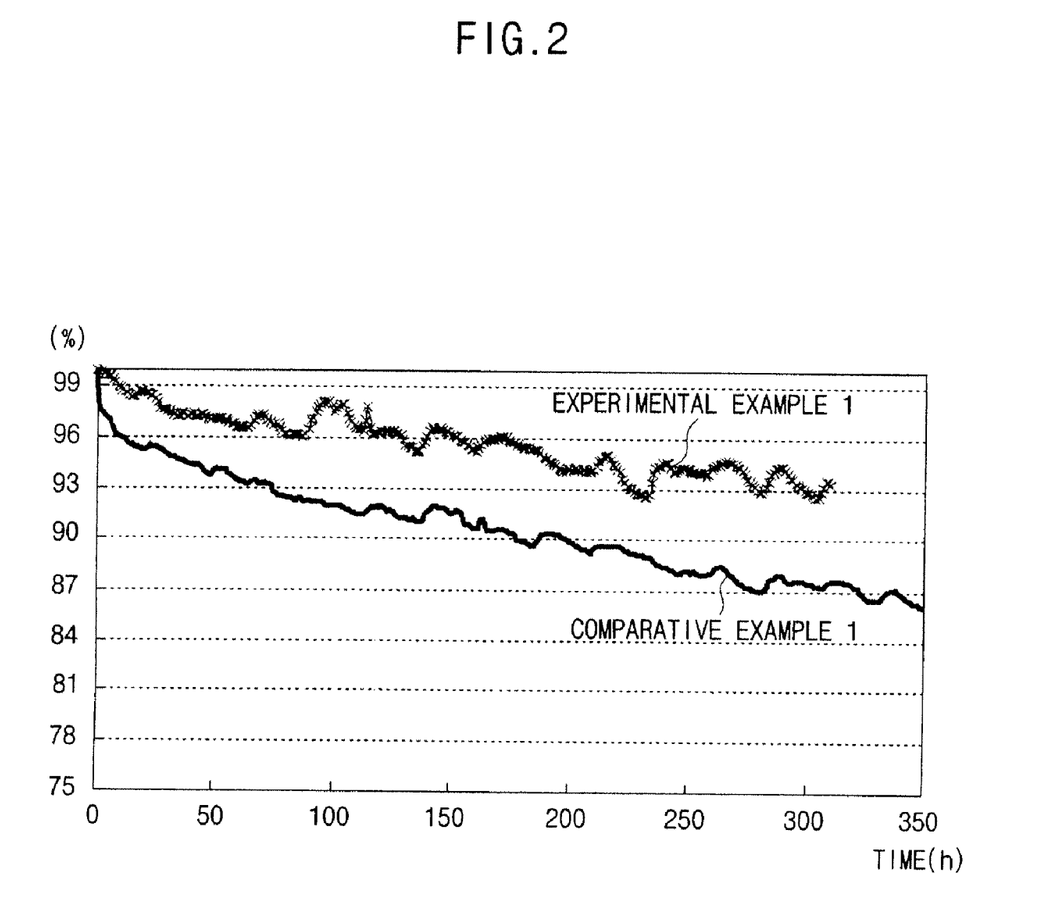
FIG. 2 is a graph comparing the lifespans of the OLEDs prepared according to Experimental Example 1 and Comparative Example 1.

In addition, a comparison of the lifespans of the OLEDs according to Experimental Example 1 and Comparative Example 1 is shown in FIG. 2. In FIG. 2, changes in luminance are graphed versus time, i.e., the x-axis of the graph is time in hours, and the y-axis is the percentage of luminance with respect to the initial luminance. Referring to FIG. 2, according to Experimental Example 1, luminance degradation was slower than Comparative Example 1. Therefore, it can be seen that the OLED according to Experimental Example 1 may have a longer lifespan than the OLED according to Comparative Example 1.

Experimental Example 2

A first electrode was formed of ITO to a thickness of about 130 nm. Thereafter, an HIL was formed of IDE-406 (obtained from Idemitsu Co.) on the first electrode to a thickness of about 210 nm, and an HTL was formed of NPB to a thickness of about 20 nm. A red EML was formed on the HTL to a thickness of about 30 nm using a mixture of CBP as a host and 8% by weight $Ir(piq)_3$ as a dopant. An ETL was formed on the red EML. Specifically, 25% by weight of sodium quinolate (which is an organic metal complex containing an alkali metal) and 75% by weight of a compound of Formula 1 were co-deposited to a thickness of about 30 nm. In the compound of Formula 1, $R_9$ is a phenyl group to which a benzimidazolyl group is bonded, and each of $R_1$ to $R_8$ and $R_{10}$ to $R_{22}$ is hydrogen.

Subsequently, a second electrode was formed on the ETL. To form the second electrode, an MgAg layer was formed to a thickness of about 16 nm, and an Al layer was formed on the MgAg layer to a thickness of about 100 nm.

Formula 1

Comparative Example 2

An OLED was prepared as in Experimental Example 2 except that the ETL was formed to a thickness of about 30 nm and included only the compound of Formula 1.

The driving voltage, current consumption, luminance, and luminous efficiency of each of the OLEDs manufactured according to Experimental Example 2 and Comparative Example 2 were measured, and the results are shown in Table 2.

TABLE 2

| | Driving voltage (V) | Current consumption (mA/cm²) | Luminance (Cd/m²) | Luminous efficiency (Cd/A) |
|---|---|---|---|---|
| Experimental Example 2 | 4.328 | 6.252 | 800 | 12.848 |
| Comparative Example 2 | 6.334 | 7.564 | 800 | 10.596 |

Referring to Table 2, the driving voltage, current consumption, and luminous efficiency at the same luminance of the OLEDs according to Experimental Example 2 and Comparative Example 2 were compared. When the ETL was formed of a mixture of the compound of Formula 1 containing benzimidazolyl (which is an aromatic heterocyclic group having 3 to 30 carbon atoms and at least one ring with two nitrogen atoms) and sodium quinolate (which is an organic metal complex containing an alkali metal), as in Experimental Example 2, driving voltage was reduced by about 2V, current consumption was reduced by about 1.3 mA/cm², and luminous efficiency was increased by about 2.25 Cd/A (about a 21% increase over the OLED according to Comparative Example 2).

Experimental Example 3

A first electrode was formed of ITO to a thickness of about 130 nm. Thereafter, an HIL was formed of IDE-406 (obtained from Idemitsu Co.) on the first electrode to a thickness of about 210 nm, and an HTL was formed of NPB to a thickness of about 20 nm. A red EML was formed on the HTL to a thickness of about 30 nm using a mixture of CBP as a host and 8% by weight $Ir(piq)_3$ as a dopant. An ETL was formed on the red EML. Specifically, 50% by weight of sodium quinolate (which is an organic metal complex containing an alkali metal) and 50% by weight of a compound of Formula 1 were co-deposited to a thickness of about 30 nm. In the compound of Formula 1, $R_9$ is a phenyl group to which a benzimidazolyl group is bonded, and each of $R_1$ to $R_8$ and $R_{10}$ to $R_{22}$ is hydrogen.

Subsequently, a second electrode was formed on the ETL. To form the second electrode, an MgAg layer was formed to a thickness of about 16 nm, and an Al layer was formed on the MgAg layer to a thickness of about 100 nm.

Formula 1

Comparative Example 3

An OLED was formed as in Experimental Example 3 except that the ETL was formed to a thickness of about 30 nm and included only the compound of Formula 1.

The driving voltage, current consumption, luminance, and luminous efficiency of each of the OLEDs manufactured according to Experimental Example 3 and Comparative Example 3 were measured, and the results are shown in Table 3.

TABLE 3

|  | Driving voltage (V) | Current consumption (mA/cm$^2$) | Luminance (Cd/m$^2$) | Luminous efficiency (Cd/A) |
| --- | --- | --- | --- | --- |
| Experimental example 1 | 4.245 | 5.689 | 800 | 14.143 |
| Comparative example 1 | 6.334 | 7.564 | 800 | 10.596 |

Referring to Table 3, driving voltage, current consumption, and luminous efficiency at the same luminance of the OLEDs according to Experimental Example 3 and Comparative Example 3 were compared. When the ETL was formed of a mixture of the compound of Formula 1 containing benzimidazolyl (which is an aromatic heterocyclic group having 3 to 30 carbon atoms and at least one ring with two nitrogen atoms) and sodium quinolate (which is an organic metal complex containing an alkali metal), as in Experimental Example 3, driving voltage was reduced by about 2.1V, current consumption was reduced by about 1.9 mA/cm$^2$, and luminous efficiency was increased by about 3.55 Cd/A (about a 33.5% increase over the OLED according to Comparative Example 3).

As described above, an ETL of an OLED is formed by co-depositing an organic metal complex including an alkali metal and a compound of Formula 1, thereby reducing driving voltage and current consumption, and increasing the luminous efficiency and lifespan of the OLED. In addition, since the ETL according to embodiments of the present invention can also have electron injection characteristics, the manufacturing process can be simplified by omitting the need to form an additional EIL.

As discussed above, an OLED according to embodiments of the present invention employs an ETL including an organic metal complex containing an alkali metal and a compound of Formula 1, thereby reducing driving voltage and current consumption and increasing luminous efficiency and lifespan. As a result, high-quality OLEDs can be achieved. In addition, since the ETL according to embodiments of the present invention can also have electron injection characteristics, the manufacturing process can be simplified by omitting the need to form an additional EIL.

Although the present invention has been described with reference to certain exemplary embodiments, it will be understood by those of ordinary skill in the art that various modifications and changes may be made to the described embodiments without departing from the spirit or scope of the present invention, as defined in the appended claims and their equivalents.

What is claimed is:

1. An organic light emitting diode (OLED) comprising:
   a first electrode;
   an organic layer on the first electrode and comprising an emission layer (EML) and an electron transport layer (ETL); and
   a second electrode on the organic layer;
   wherein the ETL comprises an organic metal complex comprising an alkali metal and a compound represented by Formula 1:

Formula 1 wherein:
   each of $R_1$ to $R_7$ and $R_{16}$ to $R_{22}$ is independently selected from hydrogen atoms, phenyl groups, indenyl groups, naphthalenyl groups, benzofuranyl groups, benzothiophenyl groups, indolyl groups, benzimidazolyl groups, benzothiazolyl groups, purinyl groups, quinolinyl groups, isoquinolinyl groups, coumarinyl groups, cinnolinyl groups, quinoxalinyl groups, azulenyl groups, fluorenyl groups, dibenzofuranyl groups, carbazolyl groups, anthracenyl groups, phenanthrenyl groups, aziridinyl groups, 1,10-phenanthrolinyl groups, phenothiazinyl groups, and pyrenyl groups, and
   at least one of $R_8$ to $R_{15}$ is an aromatic heterocyclic group having 3 to 30 carbon atoms in which at least one ring of the group has two nitrogen atoms, and each of the rest of $R_8$ to $R_{15}$ is independently selected from hydrogen atoms, phenyl groups, indenyl groups, naphthalenyl groups, benzofuranyl groups, benzothiophenyl groups, indolyl groups, benzothiazolyl groups, quinolinyl groups, isoquinolinyl groups, coumarinyl groups, azulenyl groups, fluorenyl groups, dibenzofuranyl groups, carbazolyl groups, anthracenyl groups, phenanthrenyl groups, aziridinyl groups, phenothiazinyl groups, and pyrenyl groups with the proviso that a compound in which $R_1$ to $R_8$, $R_{11}$ and $R_{12}$, and $R_{15}$ to $R_{22}$ are hydrogen atoms, and one of $R_9$, $R_{10}$, $R_{13}$ and $R_{14}$ is the aromatic heterocyclic group having 3 to 30 carbon atoms in which at least one ring of the group has two nitrogen atoms is specially excluded.

2. The OLED according to claim 1, wherein the aromatic heterocyclic group is selected from the group consisting of imidazolyl groups, benzimidazolyl groups, pyrazolyl groups, pyrazolinyl groups, pyrazolidinyl groups, oxadiazolyl groups, thiadiazolyl groups, pyridazinyl groups, pyrimidinyl groups, piperazinyl groups, purinyl groups, cinnolinyl groups, quinoxalinyl groups, and phenanthrenyl groups.

3. The OLED according to claim 1, wherein the organic metal complex is selected from lithium quinolate and sodium quinolate.

4. The OLED according to claim 1, wherein the organic metal complex is present in the ETL in an amount ranging from about 10 to about 60% by weight.

5. An organic light emitting diode (OLED) comprising:
   a first electrode;

an organic layer on the first electrode and comprising an emission layer (EML) and an electron transport layer (ETL); and a second electrode on the organic layer, wherein the ETL comprises an organic metal complex including an alkali metal and a compound represented by Formula 1:

Formula 1 wherein:
each of $R_1$ to $R_7$ and $R_{16}$ to $R_{22}$ is independently selected from the group consisting of hydrogen atoms, phenyl groups, indenyl groups, naphthalenyl groups, benzofuranyl groups, benzothiophenyl groups, indolyl groups, benzimidazolyl groups, benzothiazolyl groups, purinyl groups, quinolinyl groups, isoquinolinyl groups, coumarinyl groups, cinnolinyl groups, quinoxalinyl groups, azulenyl groups, fluorenyl groups, dibenzofuranyl groups, carbazolyl groups, anthracenyl groups, phenanthrenyl groups, aziridinyl groups, 1,10-phenanthrolinyl groups, phenothiazinyl groups, and pyrenyl groups, and at least one of $R_8$ to $R_{15}$ is a phenyl group, wherein the phenyl group is bonded to an aromatic heterocyclic group having 3 to 30 carbon atoms and at least one ring in the aromatic heterocyclic group has two nitrogen atoms, and each of the remaining of $R_8$ to $R_{15}$ is independently selected from the group consisting of hydrogen atoms, phenyl groups, indenyl groups, naphthalenyl groups, benzofuranyl groups, benzothiophenyl groups, indolyl groups, benzothiazolyl groups, quinolinyl groups, isoquinolinyl groups, coumarinyl groups, azulenyl groups, fluorenyl groups, dibenzofuranyl groups, carbazolyl groups, anthracenyl groups, phenanthrenyl groups, aziridinyl groups, phenothiazinyl groups, and pyrenyl groups.

6. The OLED according to claim 5, wherein the aromatic heterocyclic group is selected from the group consisting of imidazolyl groups, benzimidazolyl groups, pyrazolyl groups, pyrazolinyl groups, pyrazolidinyl groups, oxadiazolyl groups, thiadiazolyl groups, pyridazinyl groups, pyrimidinyl groups, piperazinyl groups, purinyl groups, cinnolinyl groups, quinoxalinyl groups, and phenanthrenyl groups.

7. The OLED according to claim 5, wherein the organic metal complex is selected from lithium quinolate and sodium quinolate.

8. The OLED according to claim 5, wherein the organic metal complex is present in the ETL in an amount ranging from about 10 to about 60% by weight.

9. The OLED according to claim 5, wherein $R_9$ is a phenyl group to which a benzimidazolyl group is bonded, and each of $R_1$ to $R_8$ and $R_{10}$ to $R_{22}$ is hydrogen.

10. A method of manufacturing an organic light emitting diode (OLED), comprising:
providing a first electrode;
forming an organic layer on the first electrode, wherein the organic layer comprises an emission layer (EML) and an electron transport layer (ETL); and
forming a second electrode on the organic layer,
wherein the ETL is formed by co-depositing an organic metal complex comprising an alkali metal and a compound represented by Formula 1:

Formula 1 wherein:
each of $R_1$ to $R_7$ and $R_{16}$ to $R_{22}$ is independently selected from hydrogen atoms, phenyl groups, indenyl groups, naphthalenyl groups, benzofuranyl groups, benzothiophenyl groups, indolyl groups, benzimidazolyl groups, benzothiazolyl groups, purinyl groups, quinolinyl groups, isoquinolinyl groups, coumarinyl groups, cinnolinyl groups, quinoxalinyl groups, azulenyl groups, fluorenyl groups, dibenzofuranyl groups, carbazolyl groups, anthracenyl groups, phenanthrenyl groups, aziridinyl groups, 1,10-phenanthrolinyl groups, phenothiazinyl groups, and pyrenyl groups, and at least one of $R_8$ to $R_{15}$ is an aromatic heterocyclic group having 3 to 30 carbon atoms in which at least one ring of the group has two nitrogen atoms, and each of the rest of $R_8$ to $R_{15}$ is independently selected from hydrogen atoms, phenyl groups, indenyl groups, naphthalenyl groups, benzofuranyl groups, benzothiophenyl groups, indolyl groups, benzothiazolyl groups, quinolinyl groups, isoquinolinyl groups, coumarinyl groups, azulenyl groups, fluorenyl groups, dibenzofuranyl groups, carbazolyl groups, anthracenyl groups, phenanthrenyl groups, aziridinyl groups, phenothiazinyl groups, and pyrenyl groups with the proviso that a compound in which $R_1$ to $R_8$, $R_{11}$ and $R_{12}$, and $R_{15}$ to $R_{22}$ are hydrogen atoms, and one of $R_9$, $R_{10}$, $R_{13}$ and $R_{14}$ is the aromatic heterocyclic group having 3 to 30 carbon atoms in which at least one ring of the group has two nitrogen atoms is specially excluded.

11. The method according to claim 10, wherein the aromatic heterocyclic group is selected from the group consisting of imidazolyl groups, benzimidazolyl groups, pyrazolyl groups, pyrazolinyl groups, pyrazolidinyl groups, oxadiazolyl groups, thiadiazolyl groups, pyridazinyl groups, pyrimidinyl groups, piperazinyl groups, purinyl groups, cinnolinyl groups, quinoxalinyl groups, and phenanthrenyl groups.

12. The method according to claim 10, wherein the organic metal complex is selected from lithium quinolate and sodium quinolate.

13. The method according to claim 10, wherein the organic metal complex is present in the ETL in an amount ranging from about 10 to about 60% by weight.

14. A method of manufacturing an organic light emitting diode (OLED), comprising:
providing a first electrode;
forming an organic layer on the first electrode, wherein the organic layer comprises an emission layer (EML) and an electron transport layer (ETL); and
forming a second electrode on the organic layer,
wherein the ETL is formed by co-depositing an organic metal complex comprising an alkali metal and a compound of Formula 1:

Formula 1 wherein:
each of $R_1$ to $R_7$ and $R_{16}$ to $R_{22}$ is independently selected from the group consisting of hydrogen atoms, phenyl groups, indenyl groups, naphthalenyl groups, benzofuranyl groups, benzothiophenyl groups, indolyl groups, benzimidazolyl groups, benzothiazolyl groups, purinyl groups, quinolinyl groups, isoquinolinyl groups, coumarinyl groups, cinnolinyl groups, quinoxalinyl groups, azulenyl groups, fluorenyl groups, dibenzofuranyl groups, carbazolyl groups, anthracenyl groups, phenanthrenyl groups, aziridinyl groups, 1,10-phenanthrolinyl groups, phenothiazinyl groups, and pyrenyl groups, and at least one of $R_8$ to $R_{15}$ is a phenyl group, wherein the phenyl group is bonded to an aromatic heterocyclic group having 3 to 30 carbon atoms and at least one ring in the aromatic heterocyclic group has two nitrogen atoms, and each of the remaining of $R_8$ to $R_{15}$ is independently selected from the group consisting of hydrogen atoms, phenyl groups, indenyl groups, naphthalenyl groups, benzofuranyl groups, benzothiophenyl groups, indolyl groups, benzothiazolyl groups, quinolinyl groups, isoquinolinyl groups, coumarinyl groups, azulenyl groups, fluorenyl groups, dibenzofuranyl groups, carbazolyl groups, anthracenyl groups, phenanthrenyl groups, aziridinyl groups, phenothiazinyl groups, and pyrenyl groups.

15. The method according to claim 14, wherein the aromatic heterocyclic group is selected from the group consisting of imidazolyl groups, benzimidazolyl groups, pyrazolyl groups, pyrazolinyl groups, pyrazolidinyl groups, oxadiazolyl groups, thiadiazolyl groups, pyridazinyl groups, pyrimidinyl groups, piperazinyl groups, purinyl groups, cinnolinyl groups, quinoxalinyl groups, and phenanthrenyl groups.

16. The method according to claim 14, wherein the organic metal complex is selected from lithium quinolate and sodium quinolate.

17. The method according to claim 14, wherein the organic metal complex is present in the ETL in an amount ranging from about 10 to about 60% by weight.

18. The method according to claim 14, wherein $R_9$ is a phenyl group to which a benzimidazolyl group is bonded, and each of $R_1$ to $R_8$ and $R_{10}$ to $R_{22}$ is hydrogen.

\* \* \* \* \*